United States Patent [19]

Span

[11] Patent Number: 4,774,411
[45] Date of Patent: Sep. 27, 1988

[54] GAMMA TOMOGRAPHY APPARATUS

[75] Inventor: Francis J. Span, Eindhoven, Netherlands

[73] Assignee: U.S. Philips Corporation, New York, N.Y.

[21] Appl. No.: 72,839

[22] Filed: Jul. 13, 1987

[30] Foreign Application Priority Data

Nov. 7, 1986 [GB] United Kingdom ............. 8626694

[51] Int. Cl.⁴ ............................................. G01T 1/166
[52] U.S. Cl. ............................................. 250/363 S
[58] Field of Search .................... 250/363 SC, 363 SF

[56] References Cited

U.S. PATENT DOCUMENTS 4,651,007 3/1987 Perusek et al. ............. 250/363 SC

Primary Examiner—Carolyn E. Fields
Attorney, Agent, or Firm—Paul R. Miller

[57] ABSTRACT

In a gamma radiography apparatus a gamma scintillation camera 1 with a rectangular scintillation plate is suspended so as to be counterbalanced and rotatable about a horizontal axis 44 for a single photon emission tomography, FIG. 1b. To enable a total body emission radiography scan to be carried out by the same apparatus, FIG. 2b, the head 1 must be turned through 90 degrees in plan view. This is effected in a compact manner by using an intermediate carrier formed by at least one of the arms 7 and 8, pivoted about a first axis 9 relative to the carrier 12. The head 1 is pivoted in the arms 7, 8, about a second axis 19 at 45 degrees to the first. A rotation of 180 degrees about both axes turns the camera field through 90 degrees.

6 Claims, 6 Drawing Sheets (i)

(ii)

(iii)

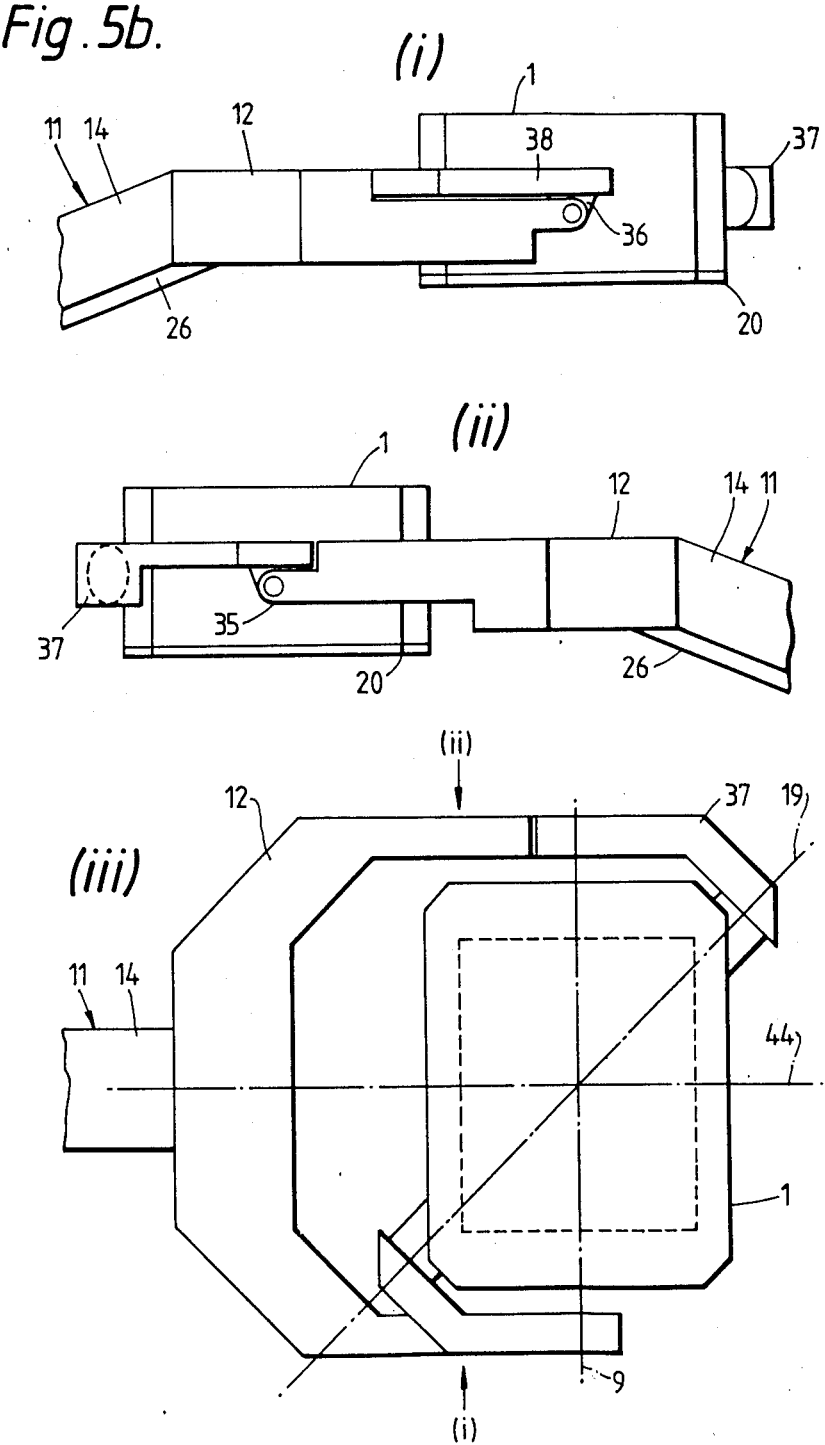

GAMMA TOMOGRAPHY APPARATUS

This invention relates to gamma radiography apparatus comprising a gamma scintillation camera head and a suspension system for supporting and positioning the gamma camera head with respect to a patient, the suspension system comprising a base, a rotatable support mounted on the base so as to be rotatable about a horizontal rotation axis, a suspension arm assembly counterbalanced at one end and pivotally mounted on the rotatable support so as to pivot in and parallel to a radial plane containing the horizontal rotation axis, the other end of the suspension arm assembly being provided with a main carrier to which the gamma scintillation camera head is pivotally connected.

An example of radiation apparatus of the kind referred to is disclosed in European Patent No. 66917.

A gamma scintillation camera head normally comprises a scintillator formed by a sheet of scintillation medium typically a thallium doped crystal of sodium iodide, an array of photodetectors typically photomultiplier tubes arranged to view corresponding overlapping regions of the scintillator, and an input collimating grid arranged in front of the scintillator to restrict and define the solid angle of incidence of the gamma radiation which reaches the scintillator. Further radiation screening is included in the camera housing substantially to prevent radiation from reaching the scintillator from directions other than via the input collimator. Such an assembly is quite massive, typically weighing about 350 kg, and therefore requires a similarly massive counterweight and suspension system, the latter typically being supported on wheels running on a linear steel track fixed to the floor to enable total body scanning to be performed on a patient supported by a support table arranged with its longitudinal axis parallel to the direction of the track.

The function of a gamma camera is to respond positionally and with directivity to gamma radiation emitted by radioactive tracer elements introduced into a patient under examination and which then accumulate in a diagnostically significant manner in localised regions of the body. The basic principles of operation of a gamma scintillation camera are explained in, for example, U.S. Pat. No. 3,011,057.

For medical diagnosis there are two distinct examination techniques employing a gamma scintillation camera. In one technique the camera is located close to the patient and is employed simply to form an image indicating the local concentration of radioactive tracer throughout the field of view by directing the camera towards a region of diagnostic interest in the patient. During a given exposure time period, the locations of successive gamma ray "events" are stored in a memory arrangement and the stored data is subsequently used to build up the output image in the form of pixels which each represent by brightness and/or colour the number of "events" occuring within the boundary of that pixel. The technique of total body scanning mentioned above represents a development of this first technique in which a number of adjacent overlapping exposures are made along the length of a patient by moving the suspension system along the track between successive exposures.

The other technique is a form of computed axial tomography referred to as single photon emission tomography (SPET). In this the gamma camera is rotated about a rotational scan axis passing longitudinally through the patient, typically the cranial-caudel axis of the patient, and is always directed radially towards the rotational scan axis. Successive exposures are carried out at regular angular intervals, the rotation being arrested during an exposure, and the stored data, i.e. that coplanar strip of pixels from each exposure field relating to a given transverse planar section, is employed to compute the respective corresponding sectional tomograms. One form of this technique is explained, for example, in U.S. Pat. No. 3,432,660 although the situation therein considered is that of rotating the patient relative to a stationary gamma camera, theoretically equivalent to the above method but less desirable from the point of view of the patient.

Historically, gamma scintillation cameras were initially provided with a circular scintillator because of manufacturing limits to the size of crystal that could be produced and the circular shape made the maximum use of the available material, but the diameter of the early scintillator was significantly less than the width of an average adult patient. Developments in crystal manufacture has now made it possible to make larger crystals, however the circular form of scintillation camera head then becomes inconveniently bulky, reducing access to the patient and greatly increasing the weight of the screening required. These disadvantages can be reduced by making the scintillator and therefore the transverse section of the field of view, rectangular, and directing the longer dimension of the rectangle across the patient. This enables the entire width of the patient to be included in the output image with the best imaging efficiency, and the rectangular shape reduces the bulkiness of the head and increases patient accessability. The fact that the field dimension of the camera along the length of the patient is not as great as that across the width, can readily be overcome by the technique of total body scanning hereinbefore referred to.

Despite the advantages of compactness, the use of a rectangular field scintillation camera head does give rise to an operational problem. This is because for a total body scan the axis of the patient lies parallel to the fixed track and therefore transverse to the rotational scan axis so that the longer dimension of the rectangular head must lie parallel to the rotational scan axis, while for a single photon emission tomography scan the axis of the patient lies parallel to the rotational scan axis so that the longer dimension of the rectangular head must lie in a plane perpendicular to the rotational scan axis.

Since it is a common requirement for a gamma camera to be capable of performing both techniques, this means that the scintillation head must be turned through 90 degrees in the usual supporting arm when changing from one operational technique to the other. To accomplish this it is possible to mount the scintillation head in a surrounding annular bearing, but such a bearing would have to be large and heavy to support the weight of the head in all the rotational positions of a tomographic scan, and the size of such a bearing would severely restrict movement and patient accessibility and would add significantly to the weight.

It is an object of the invention to provide an improved gamma scintillation camera having a rectangular scintillation detection field which can be readily adapted to perform either total body scanning or single photon emissive tomography in a compact and simple manner.

According to the invention there is provided a gamma radiography apparatus comprising a gamma scintillation camera head and a suspension system for supporting and positioning the gamma camera head with respect to a patient, the suspension system comprising a base, a rotatable support mounted on the base so as to be rotatable about a horizontal rotation axis, a suspension arm assembly counterbalanced at one end and pivotally mounted on the rotatable support so as to pivot in and parallel to a radial plane containing the horizontal rotation axis, the other end of the suspension arm assembly being provided with a main carrier to which the gamma scintillation camera head is pivotally connected, characterised in that the gamma scintillation camera has a rectangular scintillation field and is pivotally connected to the main carrier by means of an intermediate carrier which is pivotally attached to the main carrier so as to be rotatably displaceable about a first pivotal axis perpendicular to said radial plane containing the horizontal rotation axis, the gamma scintillation camera being pivotally attached to the intermediate carrier so as to be rotatable about a second pivotal axis parallel to the plane of the scintillator of the gamma scintillation camera and angularly displaced by 45 degrees from the first pivotal axis.

The intermediate carrier can be formed by a single pivoted arm or by a pair of pivoted arms which latter can be located between the side arms of a U-shaped main carrier and the camera head, or can be arranged to hinge so as to fold over into a position above or below the corresponding adjacent part of the main carrier during rotation about the first axis, so as to form a more compact arrangement.

The first and second pivotal axes are preferably arranged to pass through the centre of gravity of the camera head to ease manipulation of the head in its supports, and also to pass through the central sensing axis of the sensing field of the scintillator.

Thus gamma scintillation camera apparatus in accordance with the invention enables a rectangular scintillator head to be reoriented through 90 degrees about the axis of the field of view in a simple and compact manner which need add only a small amount of weight to the supported camera head and enables the advantages of the more compact form of a rectangular field gamma scintillation camera to be more fully realised in respect of lower equipment weight and bulk, and of improved patient accessibility. The arrangement in accordance with the invention further enables the camera head to be inclined about the longitudinal axis of a patient during a total body scan if desired.

Embodiments of the invention will now be described by way of example with reference to the accompanying drawings, of which:

FIGS. 1a and 1b illustrate respectively in side elevation and plan view apparatus in accordance with the invention arranged for SPET, FIGS. 2a and 2b similarly illustrate the apparatus of FIG. 1 arranged for total body scan, FIG. 3 illustrates the use of tilt in the arrangement of FIG. 2, and FIG. 4 illustrates a modified form of the apparatus of FIG. 1, FIGS. 5a and 5b illustrate a further embodiment of the invention, and FIG. 6 illustrates a modified form of the apparatus of FIG. 5.

FIGS. 1a and 1b illustrate a gamma scintillation camera arrangement in accordance with the invention, comprising a gamma scintillation camera head 1 and a suspension system 3 for supporting and positioning the camera head 1 with respect to a patient 43 supported on an independent patient support table 45. The suspension system which is substantially as described in European patent No. 66917 (and the equivalent U.S. Pat. No. 4,459,485), is partly enclosed in a housing 6 and comprises a base 2 on which is mounted a rotatable support 22 so as to be rotatable about a horizontal rotation axis 44, and a suspension arm assembly 11 which is counterbalanced at the end housed within the housing 6, and is pivotally mounted on the rotatable support 22 so as to pivot in and parallel to a radial plane containing the horizontal rotation axis 44.

The outer end of the suspension arm assembly 11 is connected to a main carrier 12 which in the present arrangement is U-shaped and to which the gamma scintillation camera head 1 is pivotally connected. The suspension arm assembly 11 comprises a counterbalanced main arm 14 attached to the carrier 12 by an upper pivot 10 and to the rotatable support 22 by an upper pivot 24, and an auxiliary arm 26 attached to the carrier 12 by a lower pivot 28 and to the rotatable support 22 by a lower pivot 30. This assembly forms a counterbalanced parallelogram arrangement which maintains the carrier 12 at a constant attitude as the arm assembly 11 is pivoted relative to the rotatable support 22.

In FIG. 1 the apparatus is shown in an arrangement for carrying out a single photon emission tomography scan in which the patient support table 45 supporting a patent 43 is presented to the apparatus with its longitudinal axis directed along the direction of the horizontal rotation axis 44. During an SPET scan the rotatable support 22 is rotated about the horizontal rotation axis 44 while maintaining the central axis 40 of the field of view of the camera head 1 directed radially towards the horizontal rotation axis 44.

When a total body scan is to be performed the patient support table 45 is turned through 90 degrees in a horizontal plane as indicated in FIGS. 2a and 2b. For this technique the rotatable support 22 is oriented so that the radial plane of movement of the arm assembly 11 is vertical. The camera head 1 can be arranged either above or below the patient, alternatively the support table 45 can be situated further away from the apparatus so that the camera head 1 can be directed toward the side of the patient as illustrated in FIG. 3.

In order to perform a total body scan the base 2 is supported on rollers 4 which run on linear tracks 5 fixed to the floor, and the whole apparatus 3 is displaced between exposures so that a series of overlapping gamma radiographic images are formed along the length of the patient.

The gamma scintillation camera head 1 is provided with a rectangular scintillator plate giving a rectangular field of view which is to be arranged so that the longer dimension of the rectangle is directed across the patient under examination. Thus in the case of a single photon emission tomography scan the longer dimension must be disposed at right angles to the radial plane of movement of the arm assembly 11, while for a total body scan the longer dimension of the rectangular field must be directed in or parallel to said radial plane.

It will thus be apparent that in order to change from one technique to the other it is necessary to turn the gamma scintillation camera head 1 through 90 degrees relative to the main carrier 12. This is carried out in accordance with the invention by pivotally connecting the head 1 to the main carrier 12 by means of an intermediate carrier which comprises at least one pivoted arm and in the present arrangement is represented by the pivoted arms 7 and 8 which are pivotally attached to the U-shaped main carrier 12 by outer bearings 15 and 16, respectively, so as to be rotatably displaceable about a first pivotal axis 9, perpendicular to the radial plane containing the horizontal rotation axis 44 and which represents the pivotal motion of the arm assembly 11. The gamma scintillation camera head 1 is pivotally attached to the arms 7 and 8 forming the intermediate carrier by inner bearings 17 and 18, respectively, so as to be rotatable about a second pivotal axis 19 parallel to the plane of the scintillator plate (not shown) of the camera head 1 and angularly displaced by 45 degrees from the first pivotal axis 9.

At least one of each pair of inner and outer bearings 17, 18 and 15, 16, respectively, can be provided with an associated servo drive motor, reduction gear and sensing means for indicating the angular displacement and velocity about the corresponding axis 19, 9, for displacing the camera head 1 about the first and second axes when desired, and a corresponding brake to hold the required position. These items can be of conventional construction and would normally be housed within the outer covering of the arms and are therefore not shown in the drawings.

Both the first and the second pivotal axes 9, 19, are preferably arranged to pass through the central sensing axis 40 of the sensing field of the scintillator. In order to make it easy to manipulate the camera head 1 the axes 9 and 19 should also preferably, both pass through the centre of gravity of the head 1 in its operating condition, namely with the collimator 20 attached.

In order to reorientate the rectangular camera field through 90 degrees in the apparatus in accordance with the invention, the camera head 1 is rotated once through 180 degrees in turn about each of the first and second pivotal axes 9, 19, the order and direction being immaterial except that the direction may need to be chosen to accommodate the requirements of a flexible cable link to the camera head 1. Thus the rotation about the second pivotal axis 19 will cause the orientation of the camera head 1 to be turned through 90 degrees in plan view but to end by pointing outwardly instead of inwardly towards the horizontal rotation axis 44, while the rotation about the first pivotal axis 9 will restore the camera head 1 to pointing inwardly towards the axis 44 in the new orientation. If desired, the two rotations may be effected simultaneously.

The arrangement illustrated in FIGS. 1, 2 and 3 may be modified in accordance with the invention in order to provide better access to the patient, by supporting the gamma camera head 1 on one side only. This is illustrated in FIG. 4 in which the main carrier 12 is no longer U-shaped but has only one side arm 50 to which a single pivoted arm 7 forming the intermediate carrier, is pivotally attached at one end by the outer bearing 15 so as to be rotatable about the first pivotal axis 9. The gamma camera head 1 is pivotally attached to the other end of the arm 7 by the inner bearing 17 so as to be rotatable about the second axis 19 set at 45 degrees to the first pivotal axis 9 as in FIG. 1. The inner and outer bearings 17 and 15, respectively, have in this case to be strong enough to support the entire weight of the camera head 1 and also to be capable of resisting the turning moment about a horizontal axis transverse to the respective rotation axis, which is applied by the mass of the gamma camera head 1. The side arm 50 and the pivoted arm 7 also have to be increased in strength compared with corresponding components in FIG. 1 so as to support the entire weight of the camera head 1 in the non-symmetrical manner shown. As before, servo drive motors, position sensors and brakes can be provided for each of the bearings 17 and 15, and preferably the two rotation axes 19 and 9 pass through the centre of gravity of the head 1 and the arm 7 is counterbalanced as far as possible about the axis 9 so that the corresponding servo motor (not shown) only has to overcome the inertia of the rotational assembly.

FIGS. 5a and 5b illustrate a gamma scintillation camera arrangement in accordance with the invention in which the intermediate carrier arms 37 and 38, instead of being disposed between the camera head 1 and the U-shaped carrier 12, lie either above or below the corresponding side of the carrier 12 and the bearing pivots are formed by corresponding hinges 35 and 36.

FIG. 5a(i) is a front elevation and FIG. 5a(ii) shows the rear elevation of the arrangement shown in FIG. 5a(iii).

FIG. 5b(iii) is a plan view of the camera head oriented for an SPET scan as in FIG. 1b, and FIGS. 5b(i) and (ii) are front and rear elevations respectively.

Figure 1A:
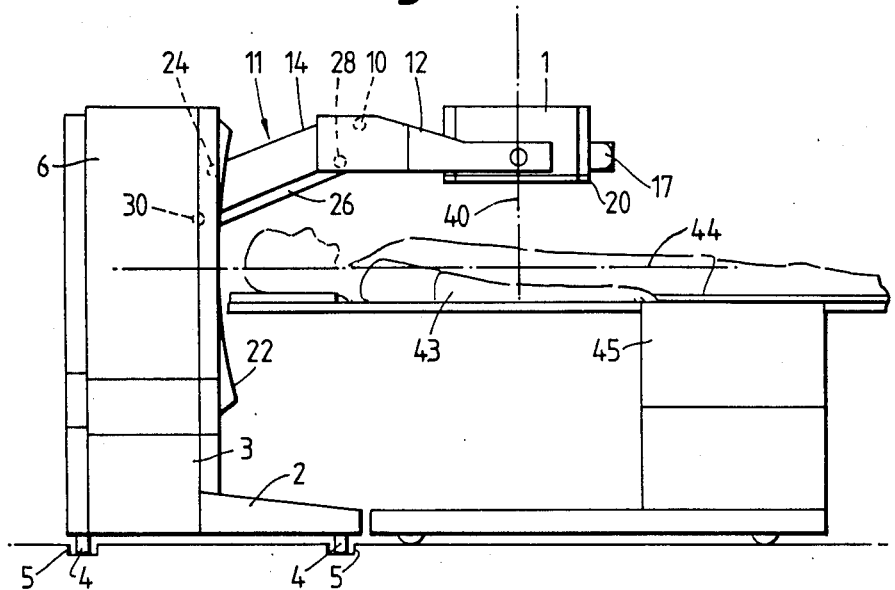
Figure 1B:
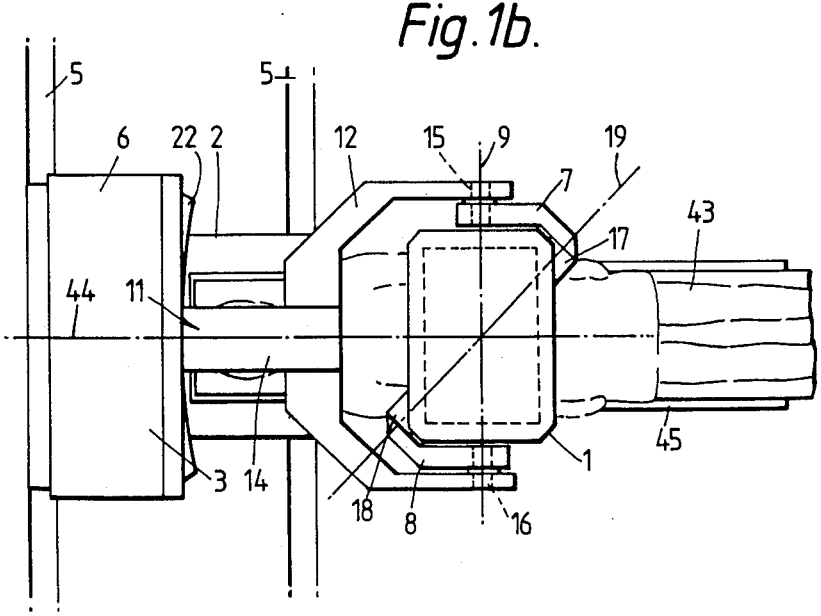
Figure 2A:
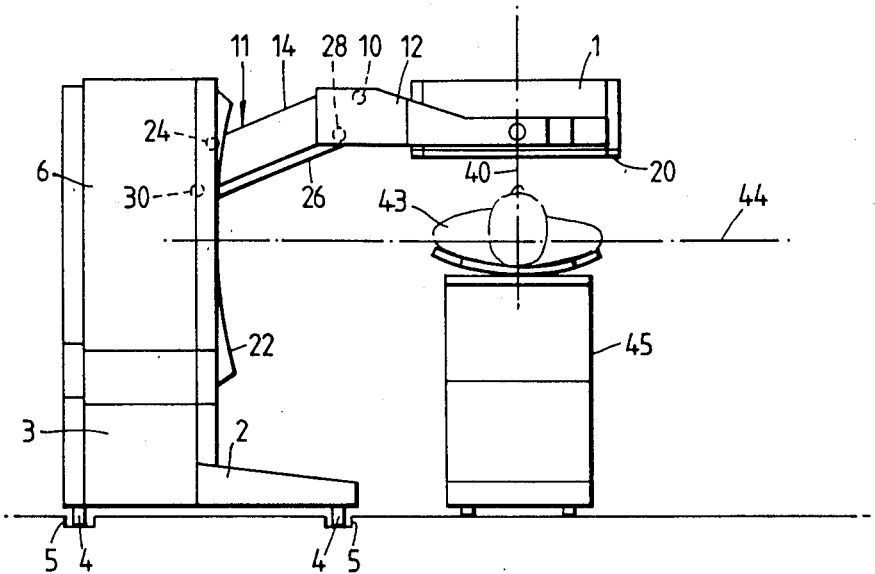
Figure 2B:
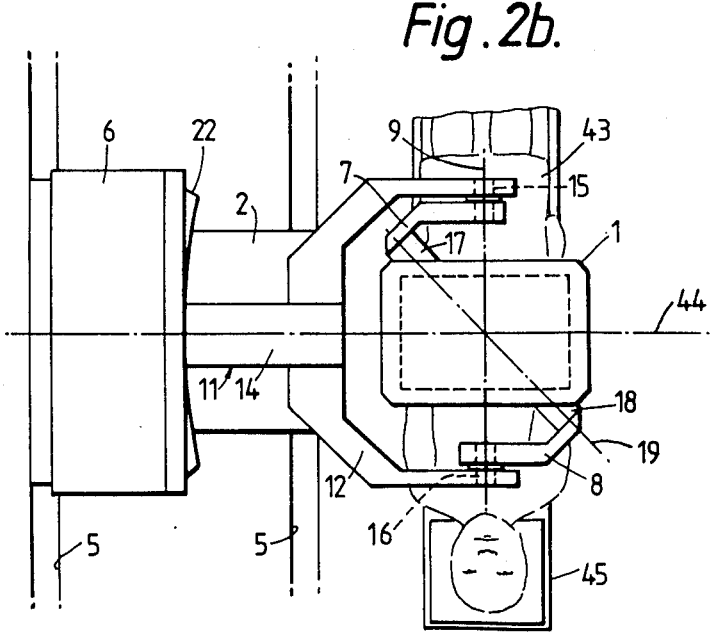
Figure 3:
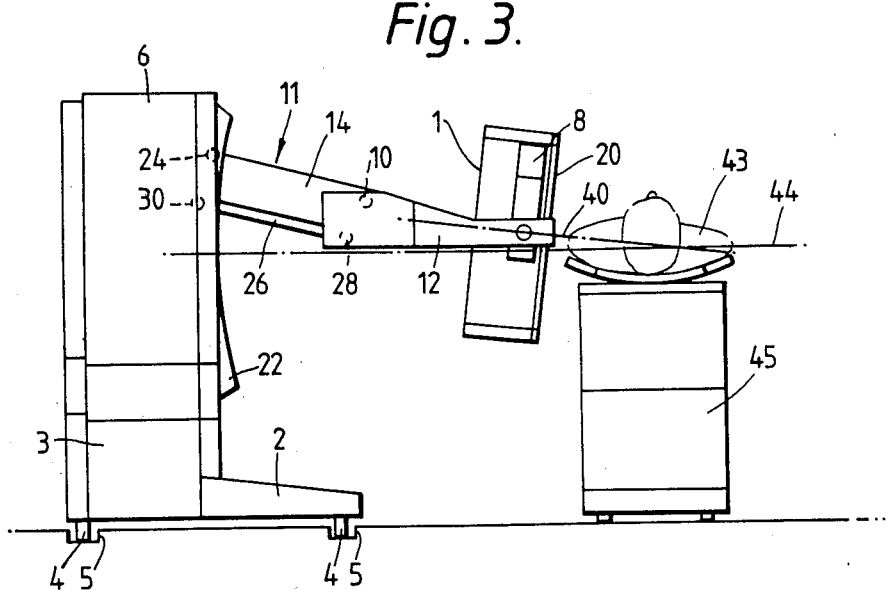
Figure 4:
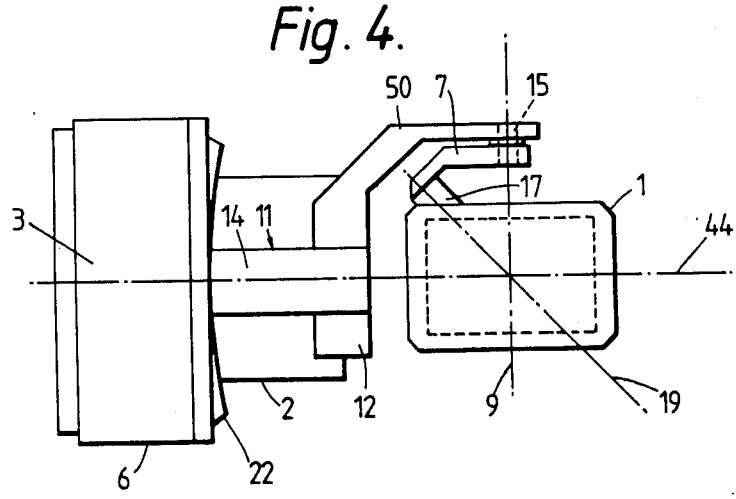
Figure 5A:
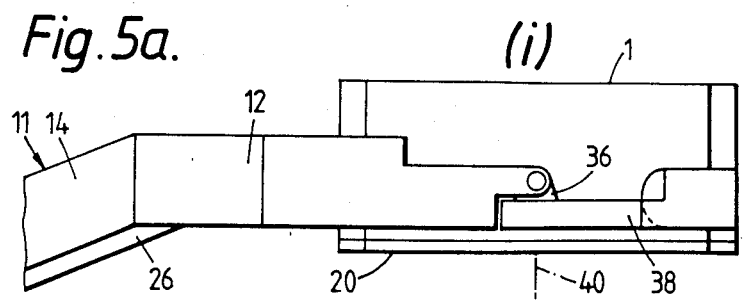
FIG. 5a(iii) is a plan view of the camera head oriented for a total body scan similar to the arrangement of FIG. 2b.
Figure 5A:
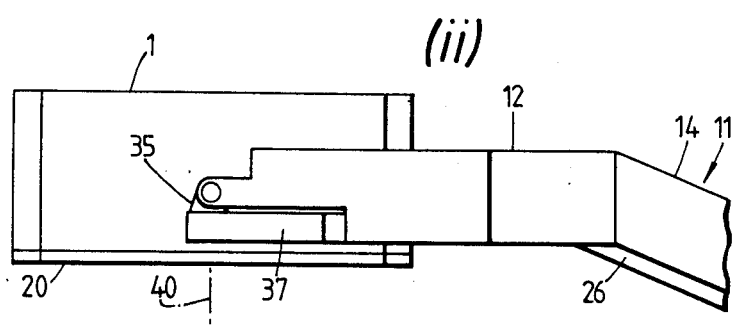
Figure 5A:
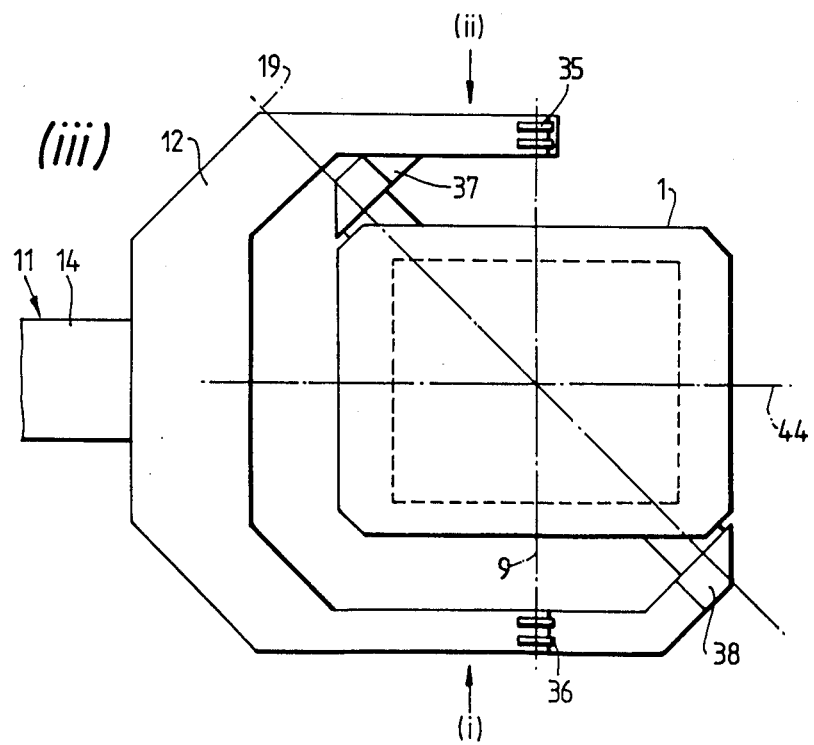

The hinged arrangement of FIGS. 5a and b has the advantage of making the head and carrier assembly more compact and therefore to give better access to the patient. It does however have a slight operating disadvantage over the other arrangement in that during a total body scan the camera head can only be tilted about the first axis for up to 180 degrees in only one direction from that in which the central axis 40 is directed radially towards the rotation axis 44. Since for reasons of supported weight, it is not economically practicable to arrange the central axis 40 of the field of view very much further from the adjacent wall of the housing 6 than about 1 m, this is not a significant disadvantage, and can be overcome by reversing the orientation of the patient support table. As in the arrangement shown in FIGS. 1, 2 and 3, at least one of the hinge pivots 35 and 36 can be provided with a servo drive motor assembly, position sensor and brake for angularly displacing and locating the arms 37 and 38 about the axis 9.

Figure 6:
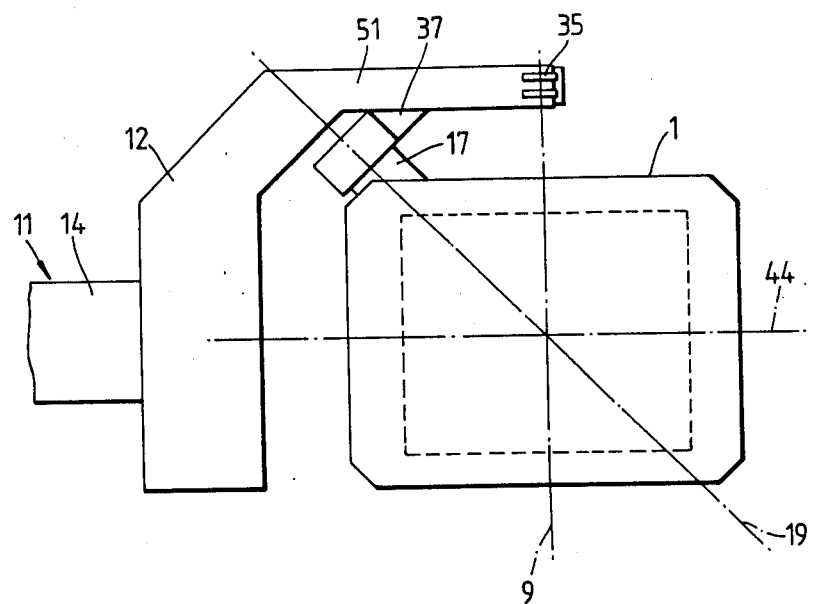

FIG. 6 illustrates the use of a main carrier 12 with one side arm 51 and an intermediate carrier comprising a single pivoted arm 37 to support the gamma camera head 1 on one side only, and employing the hinge pivot arrangement described with reference to FIGS. 5a and 5b. In this case also the arms 51 and 37 and the pivots 35 and 17 must be increased in strength relative to the corresponding parts shown in FIGS. 5a and 5b in order to form the sole and non-symmetrical support for the gamma camera head 1.

What is claimed is:

1. Gamma radiography apparatus comprising a gamma scintillation camera head and a suspension system for supporting and positioning the gamma camera head with respect to a patient, the suspension system comprising a base, a rotatable support mounted on the base so as to be rotatable about a horizontal rotation axis, a suspension arm assembly counterbalanced at one end and pivotally mounted on the rotatable support so as to pivot in and parallel to a radial plane containing the horizontal rotation axis, the other end of the suspension arm assembly being provided with a main carrier to which the gamma scintillation camera head is pivotally connected, characterised in that the gamma scintillation camera has a rectangular scintillation field and is pivotally connected to the main carrier by means of an intermediate carrier which is pivotally attached to the main carrier so as to be rotatably displaceable about a first pivotal axis perpendicular to said radial plane containing the horizontal rotation axis, the gamma scintillation camera being pivotally attached to the intermediate carrier so as to be rotatable about a second pivotal axis parallel to the plane of the scintillator of the gamma scintillation camera and angularly displaced by 45 degrees from the first pivotal axis.

2. Gamma radiography apparatus as claimed in claim 1, characterised in that the first and second pivotal axes both pass through the center of gravity of the gamma scintillation camera head.

3. Gamma radiography apparatus as claimed in claim 1 or claim 2, characterised in that the intermediate carrier comprises a single pivoted arm provided with first and second bearing portions forming respective parts of bearings arranged for rotation about the corresponding first and second axes in cooperation with corresponding bearing portions attached to the main carrier and to the gamma camera head respectively.

4. Gamma radiography apparatus as claimed in claim 3, characterised in that the or each of the bearings arranged for rotation about the first axis respectively comprise a form of hinge arranged so that the corresponding adjacent portion of the associated pivoted arm can fold back so as to lie adjacent that part of the main carrier to which it is pivotally attached.

5. Gamma radiography apparatus as claimed in claim 1 or claim 2, in which the main carrier is U-shaped and the apparatus. is characterised in that the intermediate carrier comprises a first and a second pivoted arm, each provided with first and second bearing portions forming respective parts of bearings arranged for rotation about the corresponding first and second axes in cooperation with corresponding bearing portions attached to the U-shaped carrier and to the gamma camera head respectively.

6. Gamma radiography apparatus as claimed in claim 5, characterized in that the or each of the bearings arranged for rotation about the first axis respectively comprise a form of hinge arranged so that the corresponding adjacent portion of the associated pivoted arm can fold back so as to lie adjacent that part of the main carrier to which it is pivotally attached.

* * * * *